(12) United States Patent  
Yang et al.

(10) Patent No.: US 11,324,241 B2  
(45) Date of Patent: May 10, 2022

(54) SNACK BARS AND METHODS OF MAKING

(71) Applicant: Kellogg Company, Battle Creek, MI (US)

(72) Inventors: Guoshen Yang, Battle Creek, MI (US); Jennifer Elegbede, Charlotte, MI (US); Vara Prodduk, Battle Creek, MI (US)

(73) Assignee: Kellogg Company, Battle Creek, MI (US)

( * ) Notice: Subject to any disclaimer, the term of this patent is extended or adjusted under 35 U.S.C. 154(b) by 91 days.

(21) Appl. No.: 16/357,810

(22) Filed: Mar. 19, 2019

(65) Prior Publication Data

US 2019/0289884 A1 Sep. 26, 2019

Related U.S. Application Data

(60) Provisional application No. 62/645,661, filed on Mar. 20, 2018.

(51) Int. Cl.
| | |
|---|---|
| *A23L 7/122* | (2016.01) |
| *A23L 33/135* | (2016.01) |
| *A23L 7/126* | (2016.01) |
| *A23L 7/196* | (2016.01) |
| *A23L 33/21* | (2016.01) |
| *A61K 35/747* | (2015.01) |
| *A61K 35/74* | (2015.01) |

(52) U.S. Cl.
CPC ............... *A23L 7/122* (2016.08); *A23L 7/126* (2016.08); *A23L 7/196* (2016.08); *A23L 7/1963* (2016.08); *A23L 33/135* (2016.08); *A23L 33/21* (2016.08); *A61K 35/74* (2013.01); *A61K 35/747* (2013.01); *A23V 2002/00* (2013.01); *A23Y 2220/03* (2013.01); *A23Y 2300/49* (2013.01)

(58) Field of Classification Search
CPC ........ A23L 7/122; A23L 33/135; A23L 25/25; A23L 7/126; A23L 33/21; A23V 2002/00; A23Y 2220/03; A23Y 2300/49
USPC ............................................................ 426/61
See application file for complete search history.

(56) References Cited

U.S. PATENT DOCUMENTS 5,968,365 A * 10/1999 Laurenzo ............ C08B 37/0054  
    210/641  
6,759,077 B1 * 7/2004 Lewis ..................... A23L 7/139  
    426/619

(Continued)

FOREIGN PATENT DOCUMENTS

| EP | 0862863 A2 * | 9/1998 | ............. A23K 40/30 |
| WO | 2001049131 | 7/2001 | |

(Continued)

OTHER PUBLICATIONS

Rock Doc: Designing healthier snack foods with new wheat (Year: 2014).*

(Continued)

*Primary Examiner* — Hamid R Badr  
(74) *Attorney, Agent, or Firm* — Honigman LLP

(57) ABSTRACT

Snack bars incorporating a prebiotic, probiotic and natural fibers, and methods of making such snack bars are described herein. The snack bar may incorporate waxy grains held together by a binder comprising inulin and may be enrobed with a yogurt coating. The methods may include mixing inulin into a binder syrup at low temperature and a slab-bake process for reducing water activity.

23 Claims, 3 Drawing Sheets

(56) References Cited

U.S. PATENT DOCUMENTS

Figure 1:
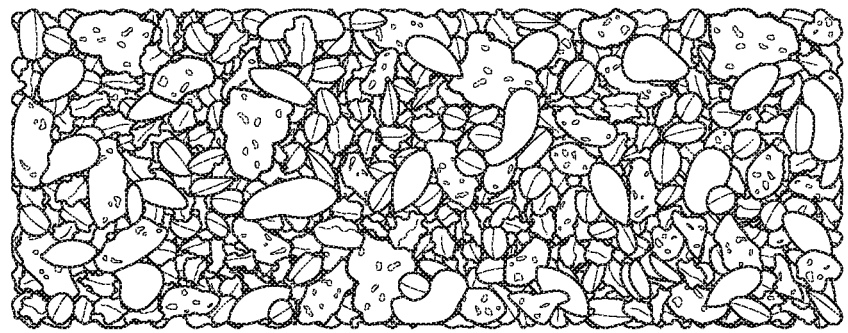

2007/0160589 A1    7/2007  Mattson
2010/0272875 A1 * 10/2010  Wilkes .................. A23L 7/122
                                                    426/541
2011/0183045 A1 *  7/2011  Froseth ................ A23L 7/122
                                                     426/93

FOREIGN PATENT DOCUMENTS

WO        2001049132        7/2001
WO    WO-2009055457 A1 *   4/2009  .............. A23G 3/48

OTHER PUBLICATIONS

PCT/US2019/022959 International Search Report dated May 28, 2019.

Heller, Lorraine, New Waxy Wheat presents innovation opportunities, Nov. 25, 2005, pp. 1-3, XP055589698, retrieved from the internet.

Peters, E. Kirsten, Rock Doc: Designing Healthier Snack Foods with New Wheat, Jul. 1, 2014, WSU Insider, XP055589763, retrieved from the internet.

Database GNPD (Online) Mintel, Feb. 3, 2017, anonymous, Chewy Yogurt Blueberry Granola Bars, XP055589718, retrieved from www.gnpd.com.

Database GNPD (Online) Mintel, Mar. 10, 2017, anonymous, Strawberries & Yogurt Flavour Granola Bars, XP055589723, retrieved from www.gnpd.com.

* cited by examiner

SNACK BARS AND METHODS OF MAKING

CROSS REFERENCE TO RELATED APPLICATION

This application claims the benefit of U.S. Provisional application No. 62/645,661, filed on Mar. 20, 2018. The entire contents of the aforementioned application are hereby incorporated by reference in their entirety.

FIELD

The present disclosure relates generally to snack bars incorporating a prebiotic, probiotic and natural fibers, as well as to methods of making such snack bars.

BACKGROUND

Snack bars, sometimes referred to as granola bars, are ready-to-eat snacks that include grain pieces held together by a binder. Consumers are increasingly desirous of snacks that provide ingredients that support digestive wellness, such as natural fiber, prebiotics and probiotics. Consumers are also desirous of snack bars with unique appearance, texture and flavor.

SUMMARY

One aspect of the invention is a snack bar comprising a waxy grain composition comprising discrete pieces of waxy grains, the waxy grain composition held together in the form of a bar by a binder comprising inulin; and a yogurt coating on the bar, the yogurt coating comprising probiotics.

In some embodiments, the waxy grain composition comprises waxy wheat, waxy barley, waxy corn, or waxy sorghum, or any combination thereof. In some embodiments, the snack bar further comprises oats held together with the waxy grain composition by the binder. In some embodiments, the binder comprises between about 10 wt % and 40 wt % inulin by weight of the binder. In some embodiments, the yogurt coating is on a first side of the snack bar. In some embodiments, the probiotic comprises *Lactobacillus acidophilus* or *Bifidobacterium lactis* or a combination thereof. In some embodiments, the snack bar has a claimable amount of total life from the probiotic of greater than or equal to about 1 billion. In some embodiments, the yogurt coating comprises *Bifidobacterium lactis* and the snack bar has a claimable amount of total life from *Bifidobacterium lactis* of greater than or equal to about 65 million.

In some embodiments, the snack bar further comprises fruit pieces held together with the waxy grain composition by the binder. In some embodiments, the snack bar further comprises nut pieces held together with the waxy grain composition by the binder. In some embodiments, the snack bar further comprises chocolate pieces held together with the waxy grain composition by the binder. In some embodiments, the snack bar further comprises seeds held together with the waxy grain composition by the binder. In some embodiments, the binder comprises a syrup.

In some embodiments, the average diameter of the discrete pieces of waxy grains is between about 4 and about 20 mm. In some embodiments, the average volume of the discrete pieces of waxy grains is between about 12 and about 600 mm³. In some embodiments, the majority of the discrete pieces of waxy grains have a diameter of between about 6 and about 16 mm and/or a volume of between about 30 and about 150 mm³. In some embodiments, pieces of oats, fruit, nuts, or chocolate, or any combination thereof, are held together with the waxy grain composition by the binder, and the pieces of oats, fruit, nuts, chocolate, or combination thereof have an average diameter between about 4 and about 16 mm and/or an average volume between about 10 and about 600 mm³.

In some embodiments, the water activity of the snack bar is below about 0.3. In some embodiments, the bar is baked at a temperature of from about 250 to about 400° F. for about 4 to about 20 minutes. In some embodiments, the bar is slab-baked at from about 250 to about 400° F. for about 4 to about 20 minutes.

Another aspect of the invention is a method of making a snack bar, comprising: mixing inulin in a syrup composition having a temperature of below about 140° F. to form a binder slurry and heating the binder slurry to above 140° F.; mixing a waxy grain composition comprising discrete pieces of waxy grains with the binder slurry; forming a slab from the mixture of the waxy grain composition and the binder slurry; and baking the slab at a temperature of from about 250 to about 400° F. for about 4 to about 20 minutes to reduce the water activity of the slab to below about 0.3.

In some embodiments, the slab is cut into bars. In some embodiments, the bars are cooled. In some embodiments, the bars are enrobed with a yogurt coating comprising probiotics. In some embodiments, the bars are bottom enrobed with a yogurt coating comprising probiotics. In some embodiments, the slab is compressed to reduce its thickness before baking. In some embodiments, probiotics are added to the yogurt coating before enrobing the snack bar with the yogurt coating, wherein at least 20 billion in total life of probiotics per snack bar are added to the yogurt coating to achieve a final total life of probiotics in the snack bar of at least 1 billion.

DRAWINGS

The drawings described herein are for illustrative purposes only of selected configurations and not all possible implementations, and are not intended to limit the scope of the present disclosure.

Figure 2:
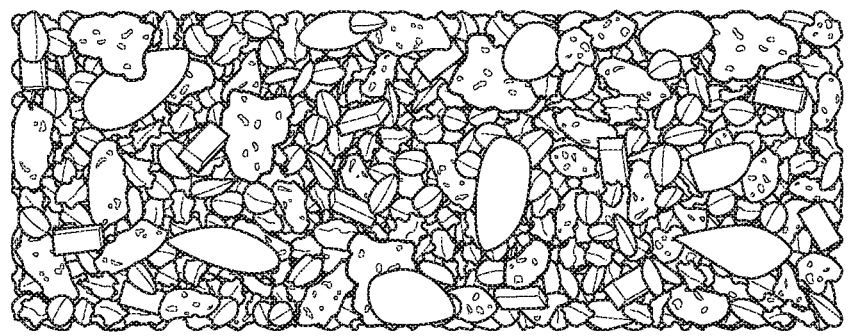
Figure 3:
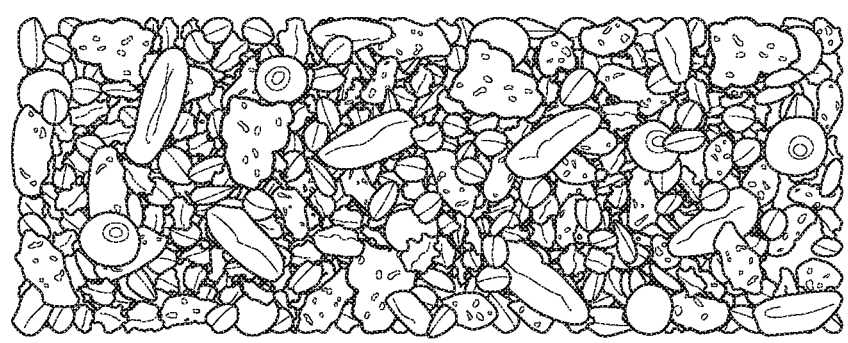
Figure 4:
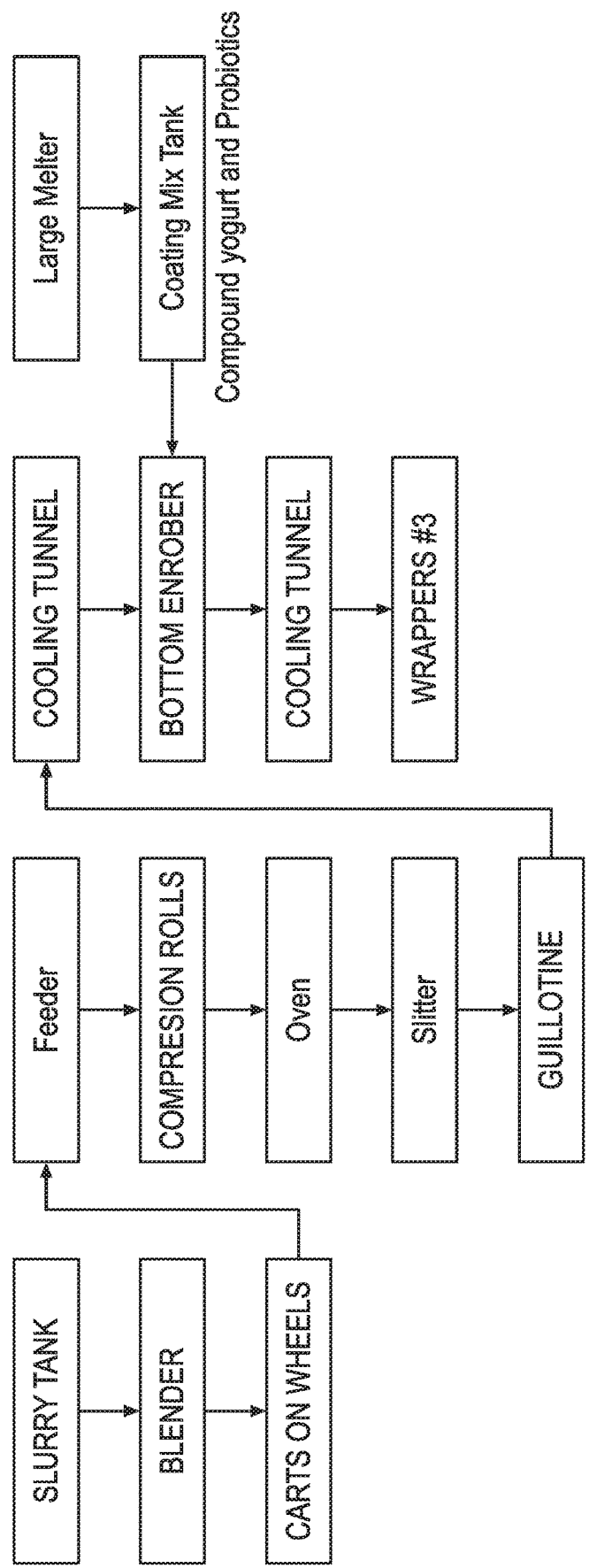
Figure 5:
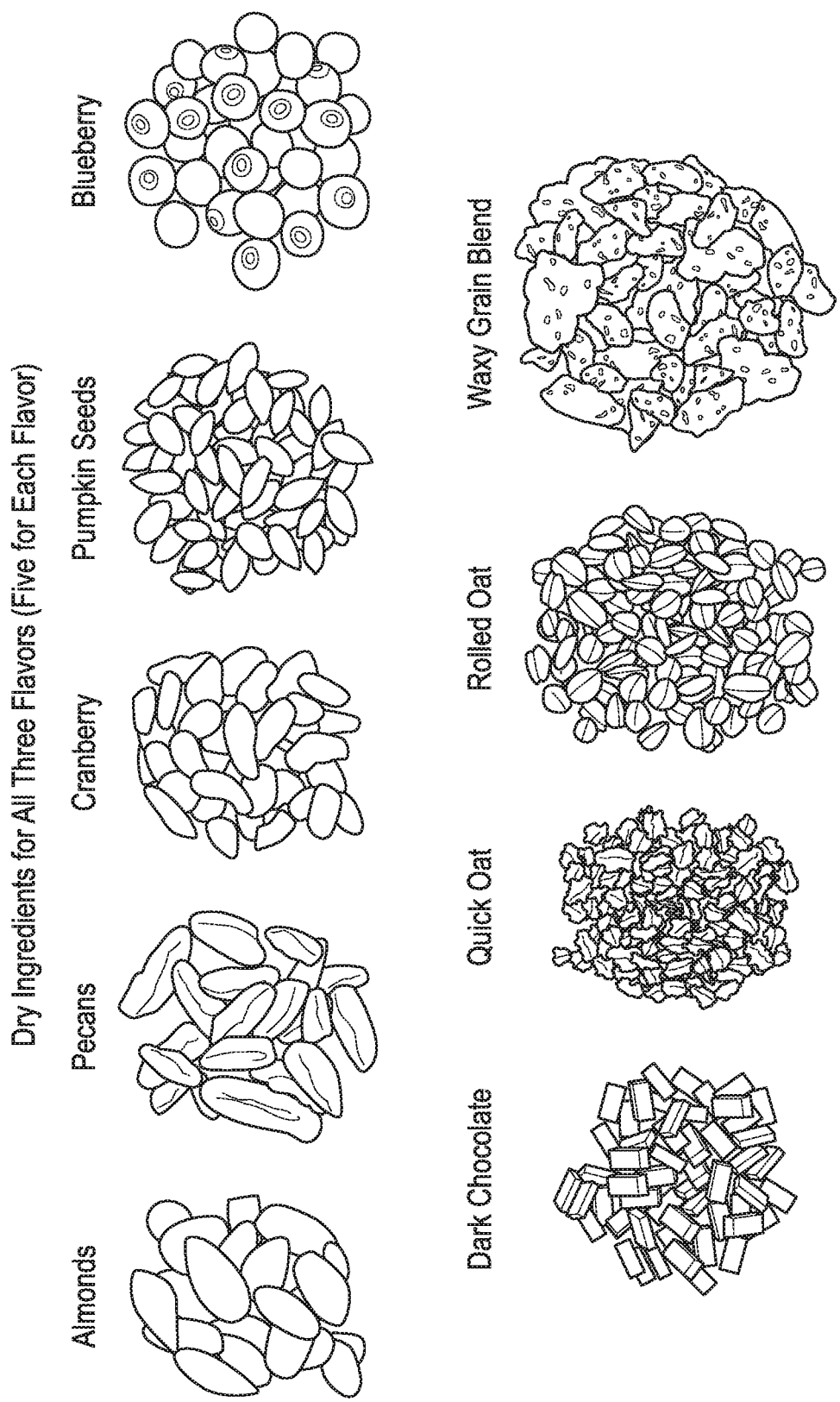

FIG. 1 is an illustration of the snack bar of Example 1.
FIG. 2 is an illustration of the snack bar of Example 2.
FIG. 3 is an illustration of the snack bar of Example 3.
FIG. 4 is a flow diagram for one embodiment of a method of making a snack bar.
FIG. 5 shows exemplary dry ingredients for incorporation into a snack bar.

DETAILED DESCRIPTION

Disclosed herein are snack bars comprising a prebiotic, probiotic and natural fiber. The combination of the power of these three ingredients together in a single snack bar supports digestive wellness. Developing a snack bar that combines these three ingredients presents certain challenges. For example, inulin, a source of prebiotic, is difficult to incorporate into a snack bar because it is difficult to incorporate a high content of inulin into binding syrup. In particular, high molecular weight inulin powder (large degree of polymerization, e.g., 30% DP 3-9, 50% DP 10-20, 20% DP 20-50) provides good prebiotic function but is difficult to mix into binding syrup. Thus, a mixing procedure has been developed to ensure thorough mixing of the inulin into the binding syrup. Also, preserving the probiotic in the snack bar (e.g., during its shelf life) can be difficult due to degradation of the probiotic when exposed to moisture. To mitigate this issue, a slab-baking process was developed to reduce the water activity of the snack bars. However, reducing water activity to avoid degradation of probiotic can be a detriment to product integrity and lead to crumbling after baking. Thus, the slab-baking process was carefully developed to reduce the water activity, while also maintaining product integrity and providing a snack bar with good texture.

In some embodiments, the snack bars described herein have unique or desirable appearance, texture and flavor. The snack bars incorporate waxy grains, optionally with whole grain oats, fruit, nuts, seeds and/or chocolate held together with a binder and coated with a yogurt coating. The waxy grains, whole grain oats, fruit, nuts, seeds and/or chocolate may be provided as discrete pieces having diameter and/or volume larger than ingredients in typical snack bars, which are often produced by a rotary molding process. In particular, the waxy grains and the baking parameters described herein provide unique or desirable appearance, texture and taste.

Turning to more of the specifics, the snack bar comprises a waxy grain composition comprising discrete pieces of waxy grains, the waxy grain composition being held together in the form of a bar by a binder comprising inulin, and a yogurt coating on the bar. The waxy grain composition provides a source of natural fiber to the snack bar. Other grains, such as whole grain oats, may also be incorporated along with the waxy grain composition as an additional source of natural fiber. The inulin in the binder provides a source of prebiotics. And the yogurt coating provides a source of probiotics to the snack bar. Together, the natural fiber, prebiotics and probiotics support digestive wellness.

The waxy grain composition comprises discrete pieces of waxy grains that are held together by the binder in the form of a bar. The waxy grains in the waxy grain composition may include waxy wheat, waxy barley, waxy corn, or waxy sorghum, or any combination thereof. In some embodiments, the waxy grains are waxy whole grains. In some embodiments, the waxy grains are cooked and/or puffed. In some embodiments, the waxy grains are flakes. To provide unique or desired appearance and texture, the size of the discrete pieces of waxy grains may be greater than in typical snack bars. Specifically, the discrete pieces of waxy grains may have an average diameter of from about 4 to about 20 mm (in some approaches, from about 6 to about 16 mm) and/or an average volume of from about 12 to about 600 $mm^3$ (in some approaches, from about 30 to about 150 $mm^3$). The discrete pieces of waxy grains may have a narrow distribution of sizes so as to provide consistently-sized pieces in the bar. For example, the majority of the discrete pieces of waxy grains may have a diameter of from about 6 to about 16 mm and/or a volume of from about 30 to about 150 $mm^3$. The waxy grains contributed to the favorable product texture, i.e., light and easy to eat. In comparison, products made with non-waxy grains had hard and tough texture.

Waxy grains and methods of making waxy grains are known in the art. For example, WO 01/49131 A1 (Kellogg Company) describes waxy wheat products and process for producing the same and WO 01/49132 A1 (Kellogg Company) describes waxy grain products and process for producing the same, each of which is incorporated by reference herein.

The waxy grain composition may be combined with other ingredients, all of which may be held together with the binder. Other grains (e.g., whole grain oats), fruit, nuts, seeds and chocolate may be incorporated into the snack bar and held together with the binder along with the waxy grain composition. As with the waxy grains, discrete pieces of the additional ingredients may be present in the snack bar and may have a size that is larger than in typical snack bars. For example, the discrete pieces (of oats, fruit, nuts, seeds, chocolate, etc.) may have an average diameter of from about 4 to about 16 mm (in some approaches, from about 6 to about 10 mm), an average volume of from about 10 to about 600 $mm^3$ (in some approaches, from about 45 to about 200 mm, and in other approaches, from about 10 to about 60 mm) and/or a majority of these discrete pieces may have a diameter of from about from about 4 to about 16 mm (in some approaches, from about 6 to about 10 mm) and/or a volume of from about 10 to about 600 $mm^3$ (in some approaches, from about 45 to about 200 mm, and in other approaches, from about 10 to about 60 mm). Advantageously, the larger pieces may make the ingredients easily identifiable by the consumer.

The snack bar comprises a binder that holds together the waxy grain composition as well as other ingredients that may be present, such as oats, nuts, fruit, seeds, chocolate, etc. The binder comprises inulin, which is a source of prebiotics. In addition, the inulin contributes to the crispy texture of the bar after baking. The binder may comprise a syrup in which the inulin may be dispersed or dissolved. For example, as detailed below, the syrup may be heated and mixed with the inulin to create a slurry for use as a binder. Advantageously, a special mixing procedure (detailed below), may be employed to mix a high content of inulin into the binder. For example, the inulin content in the binder may be from about 10 to about 40 wt % (in some approaches from about 20 to about 30 wt %, and in other approaches, from about 22 to about 27 wt %, e.g., about 22 wt %), by weight of the binder.

As described in detail below, the snack bar may be slab-baked. That is, the ingredients may be mixed with a binder and formed into a slab and then baked. The snack bar may have a low water activity, e.g., below about 0.3, which may be achieved by slab-baking. Water activity is defined as the vapor pressure of the food divided by the vapor pressure of pure water at the same temperature, and ranges from 0 to 1. The low water activity may advantageously preserve the probiotic, i.e., protecting the probiotic from degradation at higher water activity, e.g., above about 0.3. Snack bars with low water activity and methods for measuring water activity are known in the art, for example, in WO 2011/019690 A1 (Kellogg Company), incorporated by reference herein. For example, water activity may be measured by use of a commercially available water activity meter.

The snack bar comprises a yogurt coating comprising probiotics. The probiotics may include *Lactobacillus acidophilus* (LA-14) and *Bifidobacterium lactis* (HN019) from DuPont. In some embodiments, the claimable amount of total life from probiotic is greater than or equal to 1 billion, of which at least 65 million is *Bifidobacterium lactis*. Claimable amount of total life (live cultures) can be measured by the total plant count in the grown medium. The yogurt coating may be on a first side of the granola bar, e.g., the bottom side. The bottom enrobing of yogurt coating provides enhanced sensory experience to the snack bars. The yogurt coating includes yogurt or a dairy-based yogurt substitute. In some embodiments, the yogurty coating comprises Greek yogurt. The yogurt coating with minimal sourness and smooth mouthfeel is complementary to the crunchiness of the waxy grains.

Methods of making the snack bars comprise heating and dissolving inulin in a binder composition to form a binder slurry, mixing a waxy grain composition comprising discrete pieces of waxy grains with the binder slurry, forming a slab from the mixture of the waxy grain composition and the binder slurry, and baking the slab. To produce the individual snack bars, the slab is cut into bars. The bars may then be cooled. To add the yogurt coating, the bars are enrobed in a yogurt coating composition. For example, the bars may be bottom enrobed to add a yogurt coating on one side (i.e., the bottom side).

Advantageously, a high content of inulin may be mixed into the binder to provide a greater amount of prebiotics from the inulin. This is achieved by mixing the inulin into the binding syrup at a temperature below about 140° F., and slowly adding the inulin to the binding syrup. Then, the binding syrup with the added inulin is heated up to about 190° F. to completely dissolve the inulin. It has been discovered that adding inulin to the hot syrup (i.e., above about 140° F., especially closer to 190° F.) results in the inulin forming big hard lumps and the inulin will not disperse or dissolve with regular mixing equipment. Using this method, for example, the inulin content in the binder may be from about 10 to about 40 wt % (in some approaches from about 20 to about 30 wt %, and in other approaches, from about 22 to about 27 wt %, e.g., about 22 wt %) by weight of the binder.

The waxy grains (and other optional ingredients) may be slab-baked to achieve desired appearance, texture, flavor, and product integrity while reducing water activity of the snack bar. The reduced water activity helps to preserve the probiotics added via the yogurt coating, e.g., during shelf life/storage. The slab formed from the waxy grain composition and the binder slurry is baked at a temperature of from about 250 to about 400° F. (e.g., from about 300 to about 350° F.) for about 4 to about 20 minutes (e.g., for about 5 to about 10 minutes) to reduce the water activity of the slab to below about 0.3. The probiotic is well-preserved in the snack bar having water activity below about 0.3. By baking the slab in this way, it is possible to reduce the water activity while also maintaining product integrity, i.e., avoiding crumbling of the snack bar, and providing a snack bar with good texture (e.g., a crunchy, but easy to eat snack bar).

The snack bar may be enrobed with a yogurt coating comprising probiotics. To obtain 1 billion total life of probiotics for a snack bar, 20 billion of total life of probiotics per bar is added to the yogurt coating composition. By controlling the water activity of the snack bars, as described above, the probiotics in the snack bars have been shown to be stable and experience minimal loss of probiotic.

Referring to FIG. 4, a flow diagram of the method of making the snack bars is shown. At first, the slurry is made by heating and dissolving inulin and syrup ingredients. Then the dry ingredients consist of grains, nuts, fruits, etc. are mixed with slurry and almond butter. After mixing, the materials are loaded to the hopper to form the slab. The slab is compressed to the right thickness and sent to the oven on top of the oven band. After baking to desired moisture and water activity, the baked slab is cut into two inch width ropes by a slitter blades. The ropes are then cut to the bars with 4.8 inch length by Guillotine cutter. Because of slab-bake process, the ingredients such as grains, fruits, chocolate, and nuts, are more clearly visible and identifiable. After cooling, the bars are enrobed, cooled and packaged.

The practice and advantages of the disclosed embodiments may be demonstrated by the following Examples, which are presented for purposes of illustration and not limitation. Unless indicated otherwise, all amounts, percentages, and ratios of this disclosure are by weight.

EXAMPLES

Example 1

Cranberry Pumpkin Seed Snack Bar

A snack bar with cranberry and pumpkin seed pieces was prepared as described herein; i.e., waxy grains, oats, pumpkin seeds and dried diced cranberry were mixed with a slurry comprising maple syrup, brown rice syrup, inulin, canola oil, natural cranberry flavor, water, salt, sugar and rosemary extract. After mixing, almond butter was added and additional mixing was performed. The combined ingredients were formed into a slab and baked to the desired moisture and water activity. The slab was cut into pieces, cooled, and enrobed in a yogurt coating comprising Greek yogurt base, LA-14 probiotics (DuPont) and HN019 probiotics (DuPont). The ingredients and their wt % in the snack bar are provided in Table 1.

TABLE 1

Cranberry Pumpkin Seed Snack Bar Ingredients

| Dry Ingredient | | % in Dry | % in Total |
|---|---|---|---|
| | | | 49.5 |
| Rolled Oat | Viterra #5 Rolled Oat | 32 | 15.8 |
| Quick Oat | Viterra Quick Rolled Oat | 8 | 4.0 |
| Waxy Grain Crisps | California Grains | 40 | 19.8 |
| Pumpkin Seeds | Specity Foods or S. Commodity | 10 | 5.0 |
| Dried diced Cranberry | Ocean Spray | 10 | 5.0 |
| | Dry % Total | 100 | |
| Slurry | | % in slurry | 26.5 |
| Maple Syrup | Citadelle | 12.5 | 3.31 |
| Brown Rice Syrup | Domino | 38 | 10.07 |
| Inulin GR | Beneo | 22 | 5.83 |
| Canola Oil | VerraUltra | 13.2 | 3.50 |
| Natural Cranberry Flavor | | 1 | 0.27 |
| Water | | 7 | 1.86 |
| Salt | | 1.2 | 0.32 |
| Sugar | Domino | 5 | 1.33 |
| Rosemary Extract | Kalsec | 0.1 | 0.03 |
| | Slurry % Total | 100 | |
| Almond Butter | Blue Diamond | | 8.0 |
| Greek Yogurt Coating | | % in coating | 16.0 |
| Greek Yogurt Base | | 98.775 | 15.804 |
| LA-14 Probiotics | DuPont | 1.17 | 0.187 |
| HN019 Probiotics | DuPont | 0.055 | 0.009 |
| | Coating % Total | 100 | |
| | Total | | 100.0 |

The ingredient list for the cranberry pumpkin seed snack bar was as follows: waxy whole grain blend (whole: barley, wheat, corn, sorghum), whole grain oats, yogurt probiotic coating (sugar, hydrogenated palm kernel oil, milk, Greek nonfat yogurt powder [cultured skim milk; heat treated after culturing], natural flavors, *Lactobacillus acidophilus* LA-14, soy lecithin, *Bifidobacterium lactis* HN019), brown rice syrup, almond butter (almonds), inulin, pumpkin seeds, dried cranberries (cranberries, sugar), expeller pressed canola oil, maple syrup. Contains 2% or less of cane sugar, salt, natural flavors, rosemary extract for freshness.

A cranberry pumpkin seed snack bar of Example 1 is shown in FIG. 1.

Example 2

Chocolate Almond Snack Bar

A snack bar with chocolate and almond pieces was prepared as described herein with the following ingredients: waxy whole grain blend (whole: barley, wheat, corn, sorghum), whole grain oats, yogurt probiotic coating (sugar, hydrogenated palm kernel oil, milk, Greek nonfat yogurt powder [cultured skim milk; heat treated after culturing], natural flavors, *Lactobacillus acidophilus* LA-14, soy lecithin, *Bifidobacterium lactis* HN019), brown rice syrup, almond butter (almonds), inulin, almonds, expeller pressed canola oil, maple syrup, semisweet chocolate chunks (sugar, chocolate, milkfat, cocoa butter, soy lecithin, natural flavor, salt). Contains 2% or less of chocolate, cane sugar, natural flavors, salt, rosemary extract for freshness.

A chocolate almond snack bar of Example 2 is shown in FIG. 2.

Example 3

Blueberry Pecan Snack Bar

A snack bar with blueberry and pecan pieces was prepared as described herein with the following ingredients: waxy whole grain blend (whole: barley, wheat, corn, sorghum), whole grain oats, yogurt probiotic coating (sugar, hydrogenated palm kernel oil, milk, Greek nonfat yogurt powder [cultured skim milk; heat treated after culturing], natural flavors, *Lactobacillus acidophilus* LA-14, soy lecithin, *Bifidobacterium lactis* HN019), brown rice syrup, almond butter (almonds), inulin, pecans, expeller pressed canola oil, maple syrup, dried blueberries. Contains 2% or less of cane sugar, natural flavors, salt, rosemary extract for freshness.

A blueberry pecan snack bar of Example 3 is shown in FIG. 3.

Example 4

Nutritional Information

The nutritional content of the snack bars in Examples 1, 2 and 3 was determined. The nutritional information is provided in Table 2.

TABLE 2

Nutritional Information

|  | Example 1 (cranberry pumpkin seed) | Example 2 (chocolate almond) | Example 3 (blueberry pecan) |
|---|---|---|---|
| Serving Size (g) | 50 | 50 | 50 |
| Calories (kcal) | 220 | 230 | 230 |
| Total Fat (g) | 9 | 10 | 10 |
| Saturated Fat (g) | 3 | 3.5 | 3 |
| Sodium (mg) | 90 | 94 | 95 |
| Total Carbohydrates (g) | 34 | 33 | 34 |
| Dietary Fiber (g) | 7 | 7 | 7 |
| Soluble Fiber (g) | 4 | 4 | 4 |
| Insoluble Fiber (g) | 3 | 3 | 3 |
| Sugars (g) | 12 | 10 | 11 |
| Protein (g) | 5 | 5 | 5 |
| Whole Grain (g) | 21 | 20 | 20 |

Exemplary dry ingredients for the snack bars described herein are shown in FIG. 5.

Example configurations are provided above so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. A snack bar having natural fiber, prebiotics, and probiotics, the snack bar comprising a waxy grain composition comprising discrete pieces of waxy grains as the natural fiber, the waxy grain composition held together in the form of a bar by a binder comprising inulin as the prebiotics, the inulin having a high molecular weight as evidenced by 30% of the inulin having a degree of polymerization of 3 to 9, 50% of the inulin having a degree of polymerization of 10 to 20, and 20% of the inulin having a degree of polymerization of 20 to 50, and the binder having 20 to 30 weight percent of the high molecular weight inulin; and a yogurt coating on the bar, the yogurt coating comprising the probiotics; wherein the waxy grain composition comprises discrete pieces of waxy wheat, waxy barley, waxy corn, or waxy sorghum, or any combination thereof, and wherein a majority of the discrete pieces of waxy grains have a diameter of about 4 to about 20 mm and a volume of about 12 to about 600 mm³.

2. The snack bar of claim 1, further comprising oats held together with the waxy grain composition by the binder.

3. The snack bar of claim 1, wherein the yogurt coating is on a first side of the snack bar.

4. The snack bar of claim 1, wherein the probiotic comprises *Lactobacillus acidophilus* or *Bifidobacterium lactis* or a combination thereof.

5. The snack bar of claim 1, wherein the snack bar has greater than or equal to about 1 billion colony forming units (CFU) of probiotic.

6. The snack bar of claim 5, wherein the yogurt coating comprises *Bifidobacterium lactis* and wherein the snack bar has greater than or equal to about 65 million CFU of *Bifidobacterium lactis*.

7. The snack bar of claim 1, further comprising fruit pieces held together with the waxy grain composition by the binder.

8. The snack bar of claim 1, further comprising nut pieces held together with the waxy grain composition by the binder.

9. The snack bar of claim 1, further comprising chocolate pieces held together with the waxy grain composition by the binder.

10. The snack bar of claim 1, wherein the binder comprises a syrup.

11. The snack bar of claim 1, wherein the majority of the discrete pieces of waxy grains have a diameter of between about 6 and about 16 mm and/or a volume of between about 30 and about 150 mm$^3$.

12. The snack bar of claim 11, further comprising pieces of oats, fruit, nuts, or chocolate, or any combination thereof, held together with the waxy grain composition by the binder, wherein the pieces of oats, fruit, nuts, chocolate, or combination thereof have an average diameter between about 4 and about 16 mm and/or an average volume between about 10 and about 600 mm$^3$.

13. The snack bar of claim 1, wherein the water activity of the snack bar is below about 0.3.

14. The snack bar of claim 1, wherein the bar is baked at a temperature of from about 250 to about 400° F. for about 4 to about 20 minutes.

15. The snack bar of claim 14, wherein the bar is slab-baked at from about 250 to about 400° F. for about 4 to about 20 minutes.

16. The snack bar of claim 1, wherein the inulin is mixed with the binder at a temperature of below about 140° F. to form a binder slurry and then heating the binder slurry to above 140° F. to 190° F. to dissolve the inulin in the binder slurry and before adding dry ingredients to the binder slurry.

17. A method of making a snack bar, comprising:
    mixing inulin in a syrup composition having a temperature of below about 140° F. to form a binder slurry and then heating the binder slurry to above 140° F. to 190° F. to dissolve the inulin in the binder slurry and before adding dry ingredients to the binder slurry, the inulin provided by a powder and having a high molecular weight as evidenced by 30% of the inulin having a degree of polymerization of 3 to 9, 50% of the inulin having a degree of polymerization of 10 to 20, and 20% of the inulin having a degree of polymerization of 20 to 50, and the binder slurry having 20 to 30 weight percent of the high molecular weight inulin;
    mixing a waxy grain composition comprising discrete pieces of waxy grains with the binder slurry; wherein the waxy grain composition comprises discrete pieces of waxy wheat, waxy barley, waxy corn, or waxy sorghum, or any combination thereof, and wherein a majority of the discrete pieces of waxy grains have a diameter of about 4 to about 20 mm and a volume of about 12 to about 600 mm$^3$;
    forming a slab from the mixture of the waxy grain composition and the binder slurry; and
    baking the slab at a temperature of from about 250 to about 400° F. for about 4 to about 20 minutes to reduce the water activity of the slab to below about 0.3.

18. The method of claim 17, further comprising cutting the slab into bars.

19. The method of claim 18, further comprising cooling the bars.

20. The method of claim 19, further comprising enrobing the bars with a yogurt coating comprising probiotics.

21. The method of claim 20, further comprising bottom enrobing the snack bar with a yogurt coating comprising probiotics.

22. The method of claim 17, further comprising compressing the slab to reduce its thickness before baking the slab.

23. The method of claim 20, further comprising adding probiotics to the yogurt coating before enrobing the snack bar with the yogurt coating, wherein at least 20 billion CFU of probiotics per snack bar are added to the yogurt coating to achieve final probiotics in the snack bar of at least 1 billion CFU.

* * * * *